United States Patent
Zilioli et al.

(10) Patent No.: US 8,871,149 B2
(45) Date of Patent: Oct. 28, 2014

(54) MODULAR GAS CHROMATOGRAPH

(75) Inventors: Giacinto Zilioli, Rodano (IT); Stefano Pelagatti, Rodano (IT); Paolo Magni, Rodano (IT)

(73) Assignee: Thermo Fisher Scientific S.p.A., Rodano (MI) (IT)

( * ) Notice: Subject to any disclaimer, the term of this patent is extended or adjusted under 35 U.S.C. 154(b) by 371 days.

(21) Appl. No.: 13/258,678

(22) PCT Filed: Apr. 6, 2009

(86) PCT No.: PCT/IT2009/000147
§ 371 (c)(1),
(2), (4) Date: Sep. 22, 2011

(87) PCT Pub. No.: WO2010/116389
PCT Pub. Date: Oct. 14, 2010

(65) Prior Publication Data
US 2012/0006095 A1  Jan. 12, 2012

(51) Int. Cl.
*G01N 30/02* (2006.01)
*G01N 30/04* (2006.01)
*G01N 30/62* (2006.01)
G01N 30/88 (2006.01)
G01N 30/24 (2006.01)

(52) U.S. Cl.
CPC ........ *G01N 30/88* (2013.01); *G01N 2030/8881* (2013.01); *G01N 30/24* (2013.01); *G01N 2030/025* (2013.01); *G01N 30/62* (2013.01)
USPC ............................ 422/89; 73/23.42; 73/23.35

(58) Field of Classification Search
USPC .......... 73/23.41, 23.42, 23.35; 95/87; 96/104, 96/106; 422/89
See application file for complete search history.

(56) References Cited

U.S. PATENT DOCUMENTS

| | | | | |
|---|---|---|---|---|
| 3,069,894 A | * | 12/1962 | Claudy | 73/23.42 |
| 3,070,989 A | * | 1/1963 | Dueker et al. | 73/23.4 |
| 3,429,176 A | * | 2/1969 | Topham | 73/23.25 |
| 4,044,593 A | | 8/1977 | Haruki et al. | |
| 5,005,399 A | * | 4/1991 | Holtzclaw et al. | 73/23.39 |
| 5,298,225 A | * | 3/1994 | Higdon | 422/89 |
| 5,340,543 A | | 8/1994 | Annino et al. | |
| 5,611,846 A | | 3/1997 | Overton et al. | |
| 5,746,976 A | * | 5/1998 | Yamada et al. | 422/62 |
| 5,808,179 A | * | 9/1998 | Sittler et al. | 73/23.42 |
| 5,983,703 A | * | 11/1999 | Wylie et al. | 73/23.42 |
| 6,004,514 A | * | 12/1999 | Hikosaka et al. | 422/89 |
| 6,029,499 A | * | 2/2000 | Sittler et al. | 73/23.42 |
| 6,530,260 B1 | * | 3/2003 | Mustacich et al. | 73/23.41 |

(Continued)

OTHER PUBLICATIONS

Baykut, G., "Modular sampling and inlet systems for mobile environmental mass spectrometry", TRAC, Trends in Analytical Chemistry, Elsevier, Amsterdam, NL, vol. 14, No. 1, Jan. 1, 1995, pp. 10-23.

*Primary Examiner* — Lisa Caputo
*Assistant Examiner* — Punam Roy
(74) *Attorney, Agent, or Firm* — Lucas & Mercanti, LLP

(57) ABSTRACT

This invention is related to a gas chromatograph wherein more substitutable modules are foreseen, in particular injector modules and/or detector modules, as well as one embodiment in an oven module. Each module is insertable in a seat of the gas chromatograph mainframe with fast connections of its electronic and pneumatic means to corresponding outlets on said mainframe. Each module has its own heating element.

14 Claims, 7 Drawing Sheets

(56) References Cited

U.S. PATENT DOCUMENTS

| | | | |
|---|---|---|---|
| 6,598,460 B2 * | 7/2003 | Muto | 73/23.35 |
| 6,780,064 B2 * | 8/2004 | Abel et al. | 439/717 |
| 7,560,071 B2 * | 7/2009 | Nichols et al. | 422/63 |
| 8,336,366 B2 * | 12/2012 | Roques et al. | 73/23.39 |
| 8,414,832 B1 * | 4/2013 | Roques et al. | 422/89 |
| 2005/0100479 A1 * | 5/2005 | White et al. | 422/88 |
| 2006/0210441 A1 * | 9/2006 | Schmidt et al. | 422/89 |
| 2007/0089484 A1 * | 4/2007 | Bailey et al. | 73/23.42 |
| 2007/0095126 A1 | 5/2007 | Bailey et al. | |
| 2007/0204673 A1 * | 9/2007 | Bailey | 73/23.42 |
| 2008/0052013 A1 * | 2/2008 | Bailey et al. | 702/32 |
| 2008/0072976 A1 * | 3/2008 | Bailey et al. | 137/599.01 |
| 2008/0087072 A1 * | 4/2008 | Asher et al. | 73/23.42 |
| 2008/0092627 A1 * | 4/2008 | Hadley et al. | 73/23.42 |
| 2013/0218352 A1 * | 8/2013 | Iovanni et al. | 700/282 |

* cited by examiner

MODULAR GAS CHROMATOGRAPH

CROSS-REFERENCE TO RELATED APPLICATION

This application is a 371 of PCT/IT2009/000147 filed Apr. 6, 2009, the contents of which are incorporated herein by reference.

FIELD OF THE INVENTION

This invention relates to a new structure of a gas-chromatograph allowing many benefits in terms of system manufacturing, configuring and service.

DESCRIPTION OF THE PRIOR ART

A traditional gas-chromatograph is mainly constituted by an oven, housing an analytical column, an injector, for introducing the sample to be analyzed into the column inlet, and a detector connected to the column exit to detect the eluate exiting from column. The instrument is controlled by a digital/analogic control, means operating on all components and adapted to receive and handle the signals coming from the detector. In particular, the instrument control manages the temperatures of injector, oven and detector, as well as the pneumatic features of the gases fed to the injector and to the detector. Of course, the control means must be able to operate with the particular type of injector and/or detector as installed and in accordance with the instrument configuration as required by the application.

Different approaches were made in the last years to render more flexible the rigid chromatograph architecture as above described.

For instance U.S. Pat. No. 4,044,593 describes a chromatograph having removable modular analysis units fitting into a chamber within the chromatograph housing, each unit including a column, an injector and a detector, as well a block of thermally conductive material in contact with heating means of the chromatograph housing.

U.S. Pat. No. 4,057,998 relates to a chromatograph having a plurality of compartments each with temperature controlling means. Removable function modules are insertable in such compartments and may comprise injection modules, column modules, detector modules and valve modules. The function modules can be interconnected according to the analysis problem to be solved.

U.S. Pat. No. 5,686,657 shows a planar manifold assembly adapted to feed gases to an injector and a detector under the control of a pneumatic controller responsive to a computer.

U.S. Pat. No. 6,612,153 relates to a planar manifold for use in a micro or portable gas chromatograph, said manifold integrating the control pneumatics, electronic pressure controls and an injector inlet.

These and other attempts to simplify and make more easy for the end user the maintenance of a gas chromatograph did not reach up to now a success, so that actually all gas chromatographs now on the market show the rigid architecture above indicated and require a manufacturer intervention in case of failures or changes of the initial configuration. In other words, the instrument is factory completed and its configuration is factory customized with all the electronics and pneumatic devices suited for the purpose. The instrument is then tested once completed before shipment, so that the end user is allowed to change only the analytical column and other consumables.

OBJECTS OF THE INVENTION

Now, the object of this invention is to provide a new architecture for a gas chromatograph allowing to dispense for the manufacturer interventions in case of a number of failures or in case of desired change of injector and/or detector type. This new architecture further allows to have chromatograph components adapted to be tested and shipped separately, as well as kept in stock for fast replacement upgrading or change of configuration, by the same instrument end user.

SUMMARY OF THE INVENTION

The above and further objects of the invention are fulfilled by the present invention as more generally defined in the following claims.

Substantially the invention relates to a gas chromatograph formed at least in part with replaceable modules, each module comprising all means and features to be able to operate according to a pre-set configuration to fulfil the necessities of the user. Accordingly, each module comprises a corresponding functional device, for instance in the form of an injector, a detector or even an oven, related pneumatic means for feeding the required gas or gases, heating means and dedicated electronics means for controlling the pneumatic and heating means according to a pre-set configuration of the functional device.

For instance, a replaceable injector module comprises and injector body, pneumatic valves to suitably feed carrier gas to the injector body, a heater for the injector body and a dedicated electronics to control valves and the heater. The module is in the form of a single element that can be inserted in a suitable seat of the gas chromatograph mainframe and such insertion involves an electrical-electronic connection for said electronics and a pneumatic connection for the carrier gas.

In a similar way a replaceable detector module comprises a detector body, pneumatic valves to suitably feed carrier and other required gases to the detector body, a heater for the detector body and dedicated sensors and electronics to control the valves and the heater. The module is in the form of a single element that can be inserted in a suitable seat of the gas chromatograph mainframe and such insertion involves an electrical-electronic connection for said electronics and a pneumatic connection for the gases.

An oven replaceable module can be also foreseen and comprises an oven body, oven heating means, a fan and a related motor, flaps, and temperature sensing means, as well as electrical connections with the mainframe and dedicated electronic means to control the oven, electrically connected to the mainframe.

In summary, according to the invention it is foreseen a gas chromatograph mainframe wherein suitable seats with mechanical connections for the modules are formed, each seat comprising pneumatic and electric-electronic fast connections for the module, but no control means for the operation of the same module. The mainframe simply connects gas outlets with the module, for instance through locking valves which are opened at the module insertion and in similar manner connects the modules with the instrument CPU and with the instrument personal computer or user interface.

In this way the user can simply replace a module, for instance a detector o an injector module with another one having different features from those of the original one, if required, or having the same features in case of failure of the original one. This substitution can be accomplished in a very simple, fast and easy way, so that no manufacturer intervention is required. When the module is installed and connected to the pneumatics and electronics it is ready to operate without further interventions, of course after connection of the related capillary column end in the usual manner.

BRIEF DESCRIPTION OF THE DRAWINGS

A preferred embodiment of a gas chromatograph according to the invention will be now illustrated with reference to the annexed drawings in which.

DESCRIPTION OF A PREFERRED EMBODIMENT

Figure 1:
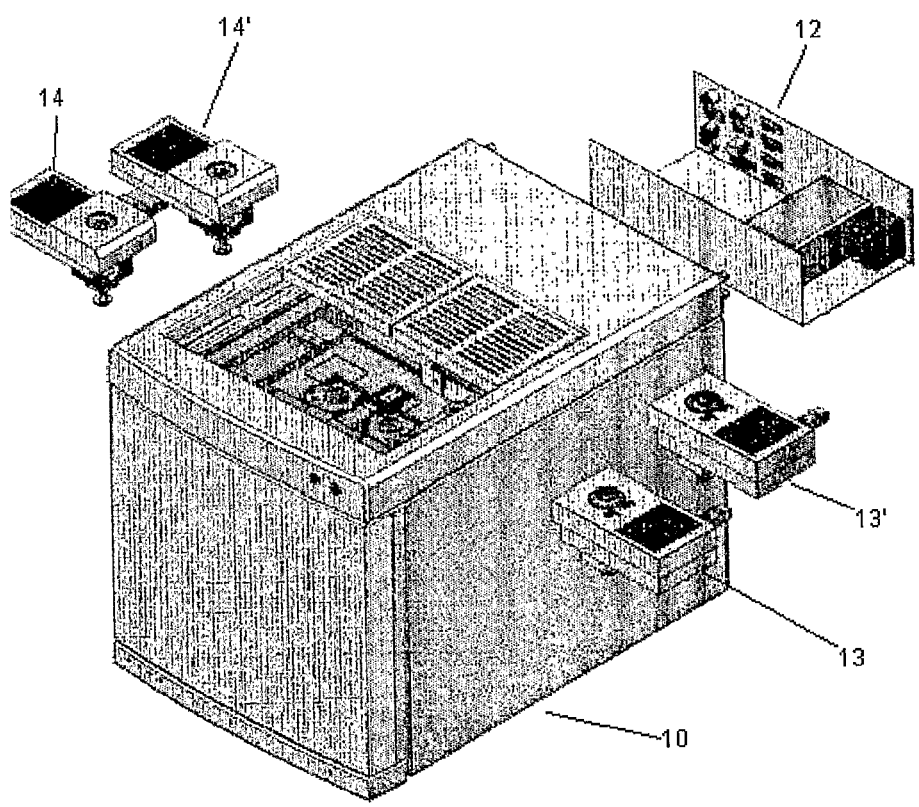
FIG. 1 is a perspective view of a gas chromatograph embodying the present invention.

The shown gas chromatograph, as indicated with reference 10 in FIG. 1, is of the general type comprising two injectors and two detectors so to be able to carry out two analyses simultaneously. This gas chromatograph is a known and conventional chromatograph, with the sole exception of the injectors and the detectors, which are in the form of modules according to the present invention. As will be described later on, the gas chromatograph may comprise also and oven made in modular form, but the shown one has the injectors and the detectors only in such modular form.

The gas chromatograph 10 has a mainframe, generally indicated with 11, housing a conventional oven with heating means, at least one fan, as well as means to control the temperature of the oven and of the capillary column or columns housed therein. The mainframe further houses a CPU for connection with a personal computer or a user interface, power supply and channels to feed gases at proper connections with the modules as diagrammatically shown in FIG. 3.

As shown in FIG. 1, the components: CPU, oven control and power supply can be placed in a support element 12 housed in the mainframe in such a manner to be easily substituted for instance in case of a CPU malfunction or different requirements of the oven control. Moreover the user interface too is housed in such a manner to be easily substitutable. The mainframe further comprises means to detachably housing two injector modules 13 and 13' and two detector modules 14 and 14' as will be described later on.

Figure 2:
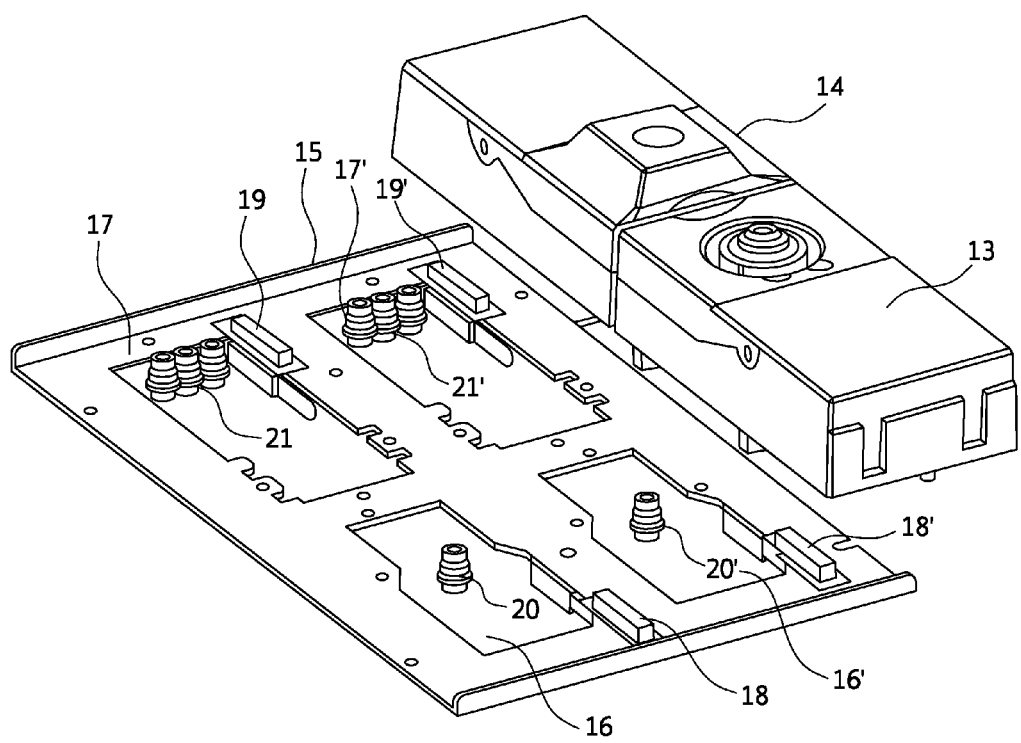
FIG. 2 is a perspective view showing a portion of the chromatograph mainframe carrying the connections for injector and detector modules.

To this end, the mainframe comprises a plate 15 (FIG. 2) wherein seats 16, 16' and 17, 17' are provided to mechanically house respectively the two injector modules 13, 13' and the two detector modules 14, 14'. The seats further house each a socket 18, 18' and 19, 19' for electric-electronic connections with the specific and dedicated electronic control means of each module with the power supply and the CPU, as well as gas connections 20, 20' and 21, 21' for feeding the required gases to each module.

Figure 3:
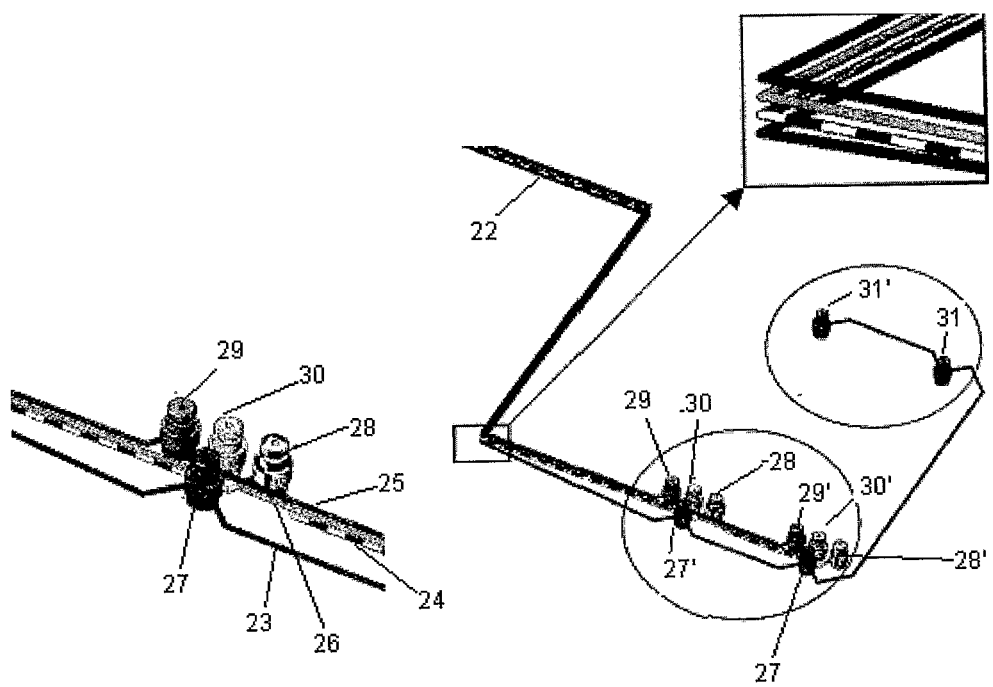
FIG. 3 is a diagrammatic view showing the gas tubing layout in the mainframe.

As best shown in FIG. 3, a plurality of ducts 22 in the mainframe 11, namely for carrier gas (duct 23,), air (duct 24), H2 or other gas for detector (duct 25) and make up gas (duct 26), feed the related gases to pneumatic connections, respectively 27, 28, 29 and 30 for the detector module and 31 for the carrier gas to the injector module. The connections 27-31 are of the fast pneumatic connection type, can have a stop valve (not shown) to intercept the gases when the related modules are not in position, and, when open, feed the related gases each at predetermined and fixed pressure and flow values.

Figure 4:
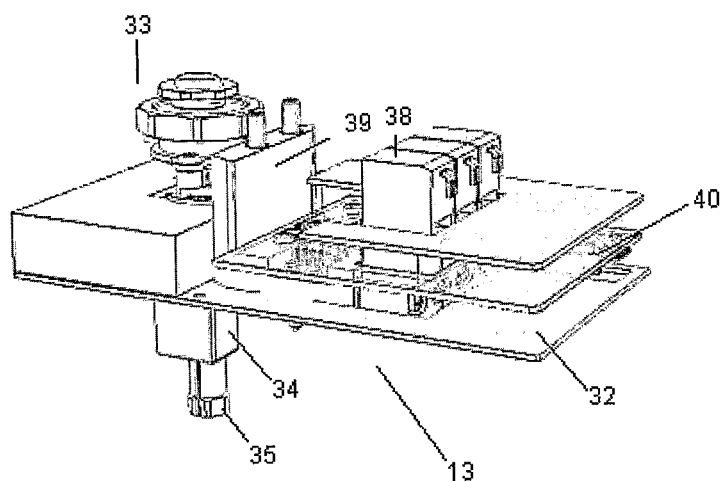
FIG. 4 is a perspective top view of an injector module.
Figure 5:
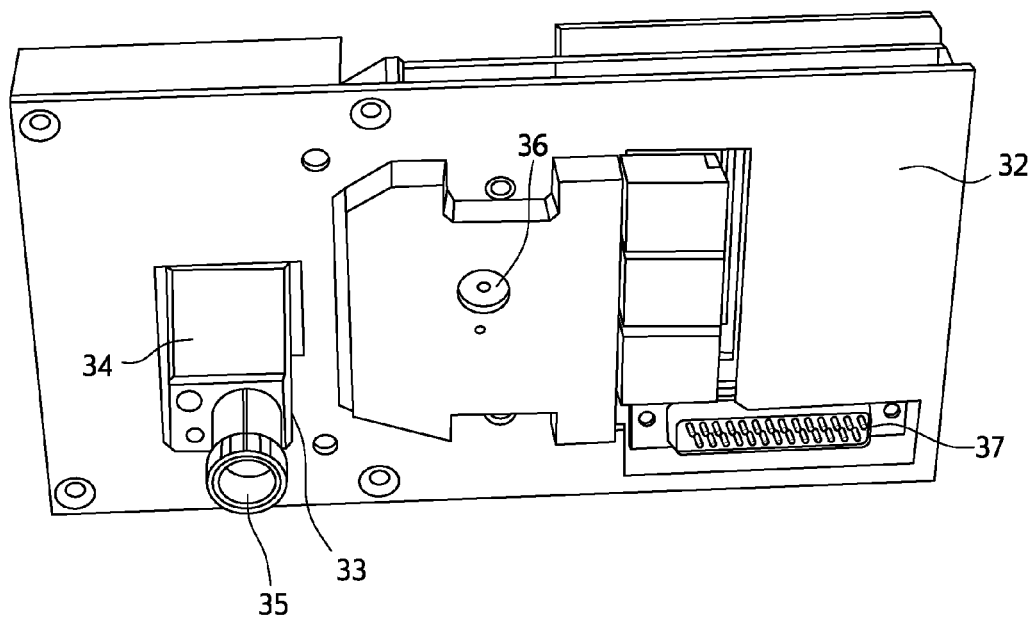
FIG. 5 is a perspective bottom view of an injector module.

FIGS. 4 and 5 show perspective views of an example of injector module 13, respectively from the top and from the bottom side. The module 13 comprises a base plate 32 carrying an injector body 33, for instance of a conventional structure, with a heater 34 and a known connector 35 for the column end. The module has a pneumatic connection 36 adapted to fit with the connection 31 for the carrier gas, as well as an electric-electronic connection 37 that can be inserted in the socket 18. The carrier gas is fed to the injector body through pneumatic valves 38 and a manifold 39, the valves being controlled, together with the heater 34, by suitable sensors and a dedicated electronic board 40, which has its hardware and software specially foreseen for the particular type of injector.

In this way, to substitute the injector with the same type of injector or with a different type of injector involves only a simple and fast substitution of the module with a new one having the required features, the new module being able to be inserted in its seat by the same user of the gas chromatograph.

Figure 6:
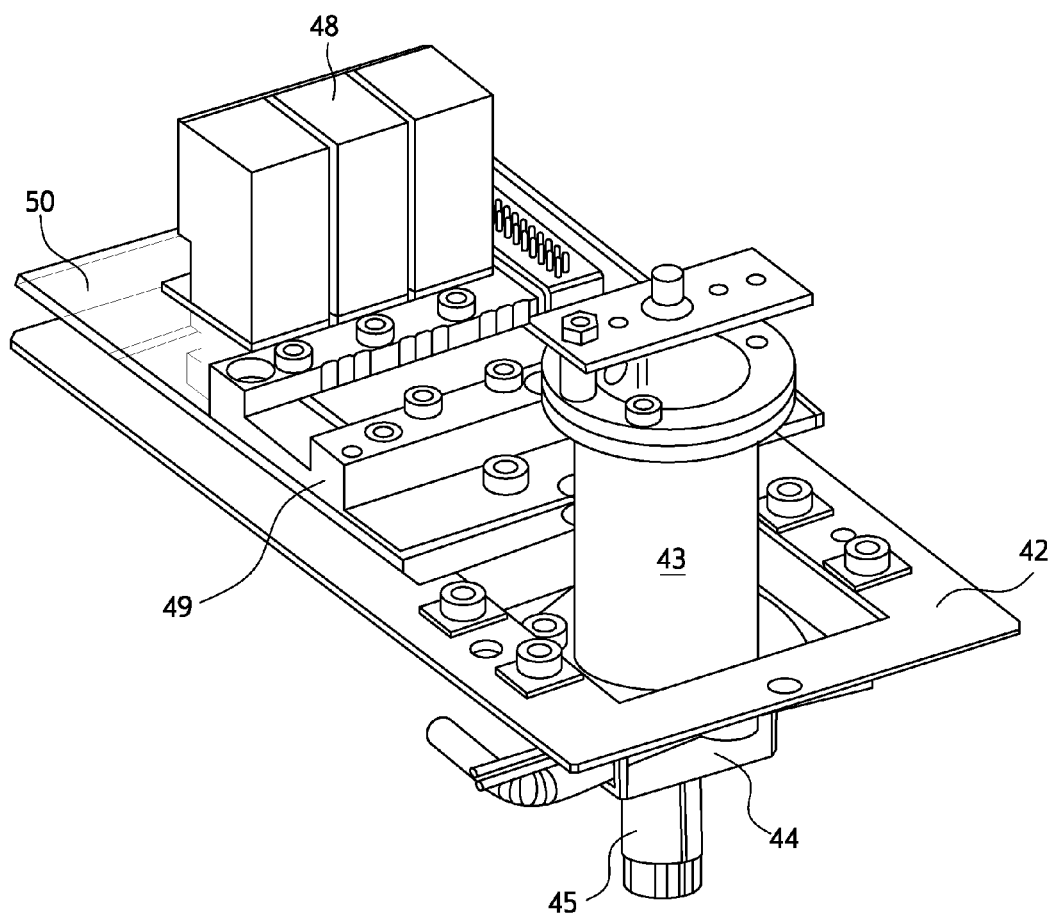
FIG. 6 is a perspective top view of an detector module.
Figure 7:
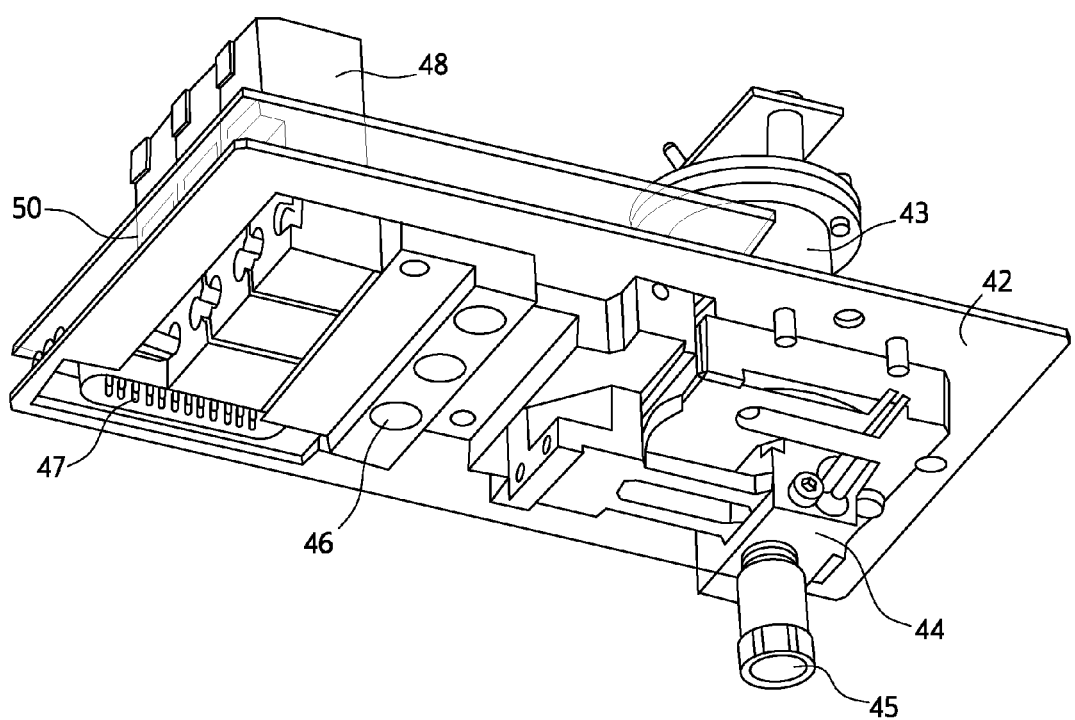
FIG. 7 is a perspective bottom view of an detector module.

FIGS. 6 and 7 show perspective views of an example of a detector module 14, respectively form the top and from the bottom side. The module 14 comprises a base plate 42 carrying a detector body 43, for instance of a conventional structure, with a heater 44 and a known connector 45 for the columns end. The module has pneumatic connections 46 adapted to fit with the connections 27-30 for the carrier gas, air, H2 and make up gas, as well as an electric-electronic connection 47 that can be inserted in the socket 19. The gases are fed to the detector body through pneumatic valves 48 and a manifold 49, the valves being controlled, together with the heater 44, by suitable sensors and a dedicated electronic board 50, which has its hardware and software specially foreseen for the particular type of detector.

In this way, to substitute the detector with the same type of detector or with a different type of detector involves only a simple and fast substitution of the module with a new one having the required features, the new module being able to be inserted in its seat by the same user of the gas chromatograph without any intervention of the manufacturer.

As soon as a new module is installed, its electronic board sends a module identification signal to the instrument CPU. The instrument CPU, on the basis of the sample type, sends to the module the target values to be obtained by the particular module.

The modules can be tested separately in factory without need of testing the assembled unit and can be shipped separately and assembled during the installation in the field, or can be kept in stock for fast replacement, upgrading or change of configuration. In this way, it is much more easy for the end user to convert the instrument to a different application requiring a different instrument configuration and in case to return to the starting configuration.

As previously said, the instrument can be designed so to incorporate a further module, i.e. an oven module. This feature is not shown in the drawings, but it can be obtained by providing a replaceable oven comprising an oven body, oven heating means, fan and motor means, flaps, and temperature sensing means, as well as electrical-electronic connections with the mainframe and dedicated electronic means to control the oven temperature, the fan operation and flap positions.

The invention claimed is:

1. A gas chromatograph comprising a mainframe housing an oven wherein at least one capillary column is installed, at least one injector, at least one detector, at least one heater and at least one electronic controller for controlling the temperature of the oven, injector(s) and detector(s), the feeding of gases to the injector(s) and detector(s) and the analysis process, wherein at least one injector and/or one detector is in a replaceable modular form, each module comprising:
- mechanical connections to said mainframe;
- pneumatic connections with gas feeding outlets on the mainframe;
- one or more connection(s) to connect the capillary column(s) end(s) to the injector or detector body of the module;
- connections with electrical-electronic outlets on the mainframe;
- a heater for the module; and
- a dedicated electronic controller for controlling at least the temperature and the gas feeding features of the module.

2. A gas chromatograph according to claim 1, wherein said pneumatic connections with gas feeding outlets on the mainframe comprise one or more pneumatic inlet connections directly insertable in corresponding gas outlets on the mainframe, the replaceable module having pneumatic valves to control the gas feedings, the pneumatic valves being controlled by said dedicated electronic controller.

3. A gas chromatograph according to claim 2, wherein a gas locking valve is disposed at each gas outlet on the mainframe.

4. A gas chromatograph according to claim 1, wherein said replaceable module is an injector module comprising an injector body, a heater for the injector body, a pneumatic connection with a carrier gas feeding outlet on the mainframe, pneumatic valves for feeding carrier gas to a manifold and injector body, as well as a dedicated electronic controller for controlling said pneumatic valves and said heater, said dedicated electronic controller being fed through an electrical-electronic connector.

5. A gas chromatograph according to claim 1, wherein said replaceable module is a detector module comprising a detector body, a heater for the detector body, pneumatic connections with carrier gas, air, make up gas and detector gas feeding outlets on the mainframe, pneumatic valves for feeding said gases to a manifold and detector body, as well as a dedicated electronic controller for controlling said pneumatic valves and said heater, said dedicated electronic controller being fed through an electrical-electronic connector.

6. A gas chromatograph according to claim 5, wherein said dedicated electronic controller is adapted to amplify and digitize the electric signal at the outlet of each detector module.

7. A gas chromatograph according to claim 1, wherein said oven is in the form of a replaceable module and comprises an oven body, oven heating means, fan and motor means, flaps, and temperature sensors, as well as electrical-electronic connections with the mainframe and a dedicated electronic controller to control the oven, electrically connected to the mainframe.

8. A gas chromatograph according to claim 1, wherein said mainframe comprises pneumatic outlets, electric-electronic outlets, a CPU and a power supply.

9. A gas chromatograph according to claim 8, wherein said CPU and connected electronic controls is mounted on said mainframe in a substitutable manner.

10. A gas chromatograph according to claim 8, wherein a personal computer or user interface module is connected to said CPU.

11. A gas chromatograph according to claim 10, wherein said user interface module is mounted on said mainframe in a substitutable manner.

12. The gas chromatograph of claim 1, wherein:
- the pneumatic connections with gas feeding outlets on the mainframe comprise fast pneumatic connections; and
- the connections with electrical-electronic outlets on the mainframe comprise fast connections.

13. A gas chromatograph comprising a mainframe housing an oven wherein at least one capillary column is installed, at least one injector, at least one detector, at least one heater and at least one electronic controller for controlling the temperature of the oven, injector(s) and detector(s), the feeding of gases to the injector(s) and detector(s) and the analysis process, wherein at least one injector and/or one detector is in a replaceable modular form, each module comprising:
- mechanical connections to said mainframe;
- connections with gas feeding outlets on the mainframe;
- one or more connection(s) to connect to the capillary column(s) end(s);
- connections with electrical-electronic outlets on the mainframe;
- a heater for the module; and
- a dedicated electronic controller for controlling at least the temperature and the gas feeding features of the module;
- wherein said replaceable module is an injector module comprising an injector body, a heater for the injector body, a pneumatic connection with a carrier gas feeding outlet on the mainframe, pneumatic valves for feeding carrier gas to a manifold and injector body, as well as a dedicated electronic controller for controlling said pneumatic valves and said heater, said dedicated electronic controller being fed through an electrical-electronic connector.

14. A gas chromatograph comprising a mainframe housing an oven wherein at least one capillary column is installed, at least one injector, at least one detector, at least one heater and at least one electronic controller for controlling the temperature of the oven, injector(s) and detector(s), the feeding of gases to the injector(s) and detector(s) and the analysis process, wherein at least one injector and/or one detector is in a replaceable modular form, each module comprising:
- mechanical connections to said mainframe;
- connections with gas feeding outlets on the mainframe;
- one or more connection(s) to connect to the capillary column(s) end(s);
- connections with electrical-electronic outlets on the mainframe;
- a heater for the module; and
- a dedicated electronic controller for controlling at least the temperature and the gas feeding features of the module;
- wherein said replaceable module is a detector module comprising a detector body, a heater for the detector body, pneumatic connections with carrier gas, air, make up gas and detector gas feeding outlets on the mainframe, pneumatic valves for feeding said gases to a manifold and detector body, as well as a dedicated electronic controller for controlling said pneumatic valves and said heater, said dedicated electronic controller being fed through an electrical-electronic connector.

* * * * *